(12) United States Patent
Suarez et al.

(10) Patent No.: US 8,801,764 B2
(45) Date of Patent: Aug. 12, 2014

(54) COSMETIC LASER TREATMENT DEVICE AND METHOD FOR LOCALIZED LIPODYSTROPHIES AND FLACCIDITY

(75) Inventors: Danilo Castro Suarez, Montevideo (UY); Wolfgang Neuberger, F.T. Labuan (MY)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 1907 days.

(21) Appl. No.: 11/415,782

(22) Filed: May 2, 2006

(65) Prior Publication Data
US 2006/0253112 A1    Nov. 9, 2006

Related U.S. Application Data

(60) Provisional application No. 60/678,096, filed on May 5, 2005.

(51) Int. Cl.
| | |
|---|---|
| *A61N 5/06* | (2006.01) |
| *A61B 18/20* | (2006.01) |
| *A61B 18/24* | (2006.01) |
| *A61B 18/00* | (2006.01) |
| *A61B 18/22* | (2006.01) |
| *A61B 17/00* | (2006.01) |

(52) U.S. Cl.
CPC .................. *A61B 18/20* (2013.01); *A61B 18/24* (2013.01); *A61B 2018/00464* (2013.01); *A61B 2018/2272* (2013.01); *A61B 2017/00792* (2013.01)
USPC .......................................................... 607/84

(58) Field of Classification Search
USPC ........ 606/9–10, 13–14, 27; 607/92–93, 2–19; 128/898
See application file for complete search history.

(56) References Cited

U.S. PATENT DOCUMENTS

| 3,538,919 A | 11/1970 | Meyer |
| 4,537,193 A | 8/1985 | Tanner |
| (Continued) | | |

OTHER PUBLICATIONS

Apfelberg et al., Progress Report on Multicenter Study of Laser-Assisted Liposuction, Aesth. Plast. Surg. 18:259-64 (1994).

(Continued)

*Primary Examiner* — Aaron Roane
(74) *Attorney, Agent, or Firm* — Bolesh J. Skutnik; BJ Associates (57) ABSTRACT

A method and device for cosmetic surgery, especially fat reduction and collagen reformation, by means of a high power laser operating at about 980 nm is presented. The cosmetic surgery method substantially reduces or removes localized lipodystrophies, and essentially reduces flaccidity by localized laser heating of adipose tissue using an optical fiber inserted into a treatment area. The method and device are particularly well suited for treating Lipodystrophies with flaccidity High power laser energy is applied to "fat" cells to breakdown the cell walls releasing the cell fluid. The laser radiation is applied through an optical fiber which may be held within a catheter-like device having a single lumen. The optical fiber may have a diffuser mounted on the tip to further apply heating to tissues surrounding the whole tip. A saline solution may also be inserted into the treatment site to aid in the heating of the fat cells and their eventual destruction as well as their removal. The pool of cell fluid in the area of treatment is removed by a combination of techniques including allowing the body to remove it by absorption and drainage from the entry sites thus minimizing trauma to the area of treatment and hastening recovery. Additional techniques to remove the cell fluid include direct force application by means of elastic bandages and external suction applied to the entry sites. Quick and lasting cosmetic changes, even in areas having prior untreatable fat tissues, are achieved while minimizing trauma to the treatment areas.

23 Claims, 7 Drawing Sheets

(56) References Cited

U.S. PATENT DOCUMENTS

| | | | |
|---|---|---|---|
| 4,686,979 | A | 8/1987 | Gruen et al. |
| 4,773,413 | A | 9/1988 | Hussein et al. |
| 4,985,027 | A | 1/1991 | Dressel |
| 5,084,043 | A | 1/1992 | Hertzmann |
| 5,102,410 | A * | 4/1992 | Dressel ............................ 606/15 |
| 5,123,845 | A | 6/1992 | Vassiliadis et al. |
| 5,129,896 | A | 7/1992 | Hasson |
| 5,188,632 | A * | 2/1993 | Goldenberg ....................... 606/7 |
| 5,334,190 | A | 8/1994 | Seiler |
| 5,370,642 | A | 12/1994 | Keller |
| 5,377,683 | A * | 1/1995 | Barken .......................... 600/439 |
| 5,395,361 | A * | 3/1995 | Fox et al. ......................... 606/15 |
| 5,470,330 | A | 11/1995 | Goldenberg et al. |
| 5,531,739 | A | 7/1996 | Trelles |
| 5,649,924 | A | 7/1997 | Everett et al. |
| 5,738,680 | A | 4/1998 | Mueller et al. |
| 5,807,385 | A | 9/1998 | Keller |
| 6,106,516 | A | 8/2000 | Massengill |
| 6,176,854 | B1 | 1/2001 | Cone |
| 6,206,873 | B1 | 3/2001 | Paolini et al. |
| 6,231,567 | B1 * | 5/2001 | Rizoiu et al. ..................... 606/10 |
| 6,283,124 | B1 * | 9/2001 | Schleuning et al. ........... 128/845 |
| 6,605,080 | B1 | 8/2003 | Altshuler et al. |
| 6,726,681 | B2 * | 4/2004 | Grasso et al. .................... 606/15 |
| 2006/0217692 | A1 * | 9/2006 | Neuberger ....................... 606/12 |
| 2006/0224148 | A1 * | 10/2006 | Cho et al. ......................... 606/15 |

OTHER PUBLICATIONS

White et al., Use of the Pulsed Nd:Yag Laser for Intraoral Soft Tissue Surgery, Lasers in Surg. and Med. 11:455-461 (1991).

Apfelberg, Results of Multicenter Study of Laser-Assisted Liposuction, Clinics in Plast. Surg. vol. 23, No. 4, 713-719 (1996).

Brochure for Sunlase Dental Laser, Sunrise Technologies, 1993 (pp. 1-10).

* cited by examiner

FIG. 1A
BEFORE

FIG. 1B
AFTER

BEFORE

FIG. 5B

AFTER

FIG. 6A

BEFORE

FIG. 6B

AFTER

COSMETIC LASER TREATMENT DEVICE AND METHOD FOR LOCALIZED LIPODYSTROPHIES AND FLACCIDITY

DOMESTIC PRIORITY UNDER 35 USC 119(E)

This application claims the benefit of U.S. Provisional Application Ser. No. 60/678,096, filed May 5, 2005, which is incorporated by reference herein.

BACKGROUND OF THE INVENTION

1. Field of the Invention

The present invention relates to the field of cosmetic surgery and, in particular, relates to laser surgery to remove excess adipose cells in areas of the body prone to buildup of such tissues and further these areas are not amenable to long term removal of these tissues by exercise and/or diets.

2. Invention Disclosure Statement

It is a well known fact that modern society has created an abundance of readily available foods, i.e., "fast food," and also created an environment where entertainment has fostered a sedentary life style of, for example, watching television, playing video games and talking on the phone while eating high caloric snack foods. This has allowed people to gain excessive weight by an increase in adipose tissue, fat cells. Certain heredity conditions further have also created areas of excessive fat cells that are difficult to remove in that they are in areas that are not affected or minimally affected by diet and exercise.

Excessive fat depositions or "lipodystrophies" are produced by a disproportionate increase in the deeper section of the subcutaneous cellular tissues.

Lipodystrophies are produced because the adiposities have a hereditary genetic code which makes them evolve in a specific way. Each adipocite cell has Beta 1 (lipogenetic) and Alfa 2 (lipolitic) receptors in its membrane. When there are more Beta 1 receptors on a particular area, then a localized obesity or lipodystrophy is produced. Because of the excessive Beta receptors in certain families, these families have a tendency for enlarged legs, breasts, waists, etc. On these patients treatment with low caloric diets exclusively is normally not successful which leads to abandonment of the treatment and recovering whatever localized fat was removed and returning to the same unhealthful practices.

The only effective way to treat lipodystrophies is to directly act on the genetically altered fat tissues and similar tissues in the area of treatment.

Historically, different methods have been developed to treat this problem and billions of dollars are being spent annually by people to remove or reduce fat tissue. By the late 70's liposuction started to be used followed by liposculpture in the late 80's being an improved liposuction performed under local anesthesia using traumatic trocars to remove fluids. Later ultrasonic liposculpture was developed by mid 90's and there are some reports on "laser liposuction" (using an external laser source) which is not clearly proved to be effective so far.

Some patents of interest are:

U.S. Pat. No. 5,807,385 by Keller, titled Method of Laser Cosmetic Surgery, discloses cosmetic laser surgery for eliminating wrinkles, frowns, and folds, for example. A quartz fiber is inserted into the skin and laser radiation in the range from 532 to 1060 nm is noted with a preferred wavelength of 532 nm. The use of various medical devices for removing wrinkles and other unwanted features such as hooks, retractors, bivalve speculum, etc., is noted.

U.S. Pat. No. 6,106,516 by Massengill, titled, "Laser-Assisted Liposuction Method and Apparatus," discloses a liposuction cannula having a lumen from a source of water, a means for suction for removing the water, and a laser source within the cannula for heating the water in an active area of the tip of the cannula. The heated water leaves the tip and heats the surrounding fatty tissue to a point of liquefaction. The laser radiation does not directly affect any tissue.

U.S. Pat. No. 6,206,873 by Paolini, et al., titled, "Device and Method for Eliminating Adipose Layers by Means of Laser Energy," discloses a hollow needle with an optical fiber in the center. The fat tissues, adipose cells, are liquidized when the cell walls are broken. The fluid is removed by suction through the needle. Laser wavelength range is noted as from 0.75 to 2.5 microns but a preferred wavelength of 1.06 is called out. A rounded optical fiber end is shown in FIG. 3 beyond the needle end. Paolini et al. use a Nd:YAG type of laser and note a wavelength range above. Paolini et al. further note that the liquid produced may be removed from the body by normal absorption, etc. Col. 4, lines 32 to 39.

U.S. Pat. No. 6,605,080 by Altshuler et al., titled, "Method and Apparatus for the Selective Targeting of Lipid-Rich Tissues," discloses the removal of lipid rich tissue. The external laser, a YAG source as well as other lasers, output energy with a wavelength range of 880 to 935 nm, 1150 to 1230 nm or 2280 to 2360. It notes that the radiation in the lower band, for example, 900 to 930, and 1150 to 1230, may be preferred in the treatment of fat tissue. Col. 11, line 55 to Col. 12, line 9. The laser light is applied externally and suction by cannula or hypodermic needle may be used to remove the lipid tissue that has been destroyed and formed into liquid. Col. 12, lines 30 to 55. Also, cooling to the skin tissue is noted. Col. 11, lines 1 to 22. The danger of using internal laser energy to remove fat tissue is noted on Col. 6, lines 50 to 64, because of the high power required.

There is thus a need for a treatment technique that minimizes surface distortion, post operative complications, and removes adipose cells in selected areas. The present invention satisfies that need.

OBJECTIVES AND BRIEF SUMMARY OF THE INVENTION

It is an object of the present invention to provide a method of cosmetic surgery using laser radiation applied by an optical fiber to an area of treatment.

It is another object of the present invention to provide a method of cosmetic surgery using laser radiation for the destruction of fat tissue in the area of treatment.

It is a further object of the present invention to provide a method of cosmetic surgery using laser radiation of a wavelength of about 980 nm.

It is a still further object of the present invention to provide a method of cosmetic surgery using laser radiation that directly affects the fat tissues to destroy the targeted adiposities.

It is at least one aim of the present invention is to provide a method of cosmetic surgery using laser radiation from a high power source to quickly heat targeted tissue for destruction.

It is another aim of the present invention to provide a method of cosmetic surgery using laser radiation that directly affects the fat tissues especially in areas of the body resistant to diet and exercise.

It is also another aim of the present invention to provide a method of cosmetic surgery using laser radiation that directly affects the sub-dermal fatty tissues.

It is at least one goal of the present invention to provide a method of cosmetic surgery using laser radiation that directly affects adiposite causing emulsification of the fatty tissue and then elimination by absorption, removal by the lymphatic system and by drainage.

It is another goal of the present invention to provide a method of cosmetic surgery using laser radiation that directly affects the fat tissues without destruction of the structural tissues.

It is a further goal of the present invention to provide a method of cosmetic surgery using laser radiation that reduces skin flaccidity by up to 50% or more.

It is also a further goal of the present invention to provide a method of cosmetic surgery using laser radiation that directly affects cellulites resulting in strengthening and flatness to the skin affected by the laser treatment.

Briefly stated, the present invention provides a method and device for cosmetic surgery, especially fat reduction and collagen reformation, by means of a high power laser operating at about 980 nm. The cosmetic surgery method substantially reduces or removes localized lipodystrophies, and essentially reduces flaccidity by localized laser heating of adipose tissue using an optical fiber inserted into a treatment area. The method and device are particularly well suited for treating Lipodystrophies with flaccidity High power laser energy is applied to "fat" cells to breakdown the cell walls releasing the cell fluid. The laser radiation is applied through an optical fiber which may be held within a catheter-like device having a single lumen. The optical fiber may have a diffuser mounted on the tip to further apply heating to tissues surrounding the whole tip. A saline solution may also be inserted into the treatment site to aid in the heating of the fat cells and their eventual destruction as well as their removal. The pool of cell fluid in the area of treatment is removed by a combination of techniques including allowing the body to remove it by absorption and drainage from the entry sites thus minimizing trauma to the area of treatment and hastening recovery. Additional techniques to remove the cell fluid include direct force application by means of elastic bandages and external suction applied to the entry sites. Quick and lasting cosmetic changes, even in areas having prior untreatable fat tissues, are achieved while minimizing trauma to the treatment areas.

The above, and other objects, features and advantages of the present invention will become apparent from the following description read in conjunction with the accompanying drawings, (in which like reference numbers in different drawings designate the same elements).

DETAILED DESCRIPTION OF THE PREFERRED EMBODIMENTS

The present invention describes a method and device for cosmetic surgery by means of a high power laser operating at about 980 nm. The cosmetic surgery method substantially reduces or removes localized lipodystrophies and/or flaccidity by localized heating of adipose tissue by means of an optical fiber inserted into an area of treatment. The high power laser energy is applied to heat the "fat" cells to a temperature wherein the cell walls break releasing the cell fluid. The laser radiation is applied by an optical fiber and the optical fiber may be held within a catheter-like device having a single lumen therein. The optical fiber may have a diffuser mounted on the tip to facilitate heating tissues surrounding the whole tip. To further aid in heating of the fat cells, a saline solution is infused into the treatment site. The pool of cell fluid in the area of treatment may be removed by a combination of techniques including allowing the body to eliminate it by absorption and/or removal, drainage from the entry sites thus minimizing trauma to the area of treatment, direct force application by means of elastic bandages and external suction applied to the entry sites. The method and devices of the present invention provide for quick and lasting cosmetic changes in areas having prior untreatable fat tissues while at the same time minimizing trauma to the areas of treatment.

In one embodiment the technique uses a 15 w-980 nm diode laser to rid the patient of aesthetically unpleasing fat and reduce flaccidity on different parts of the body, especially in areas that are resistant to change by dieting and exercising.

The treatment with the 980 nm laser proved to be efficient and more suitable rather than traditional liposuction on up to 80% of the patients. Each adiposite has a fat content which is emulsified by the laser action and then absorbed and eliminated via lymphatic system. Lipids are formed by a Glycerol chain and 3 units of 3-fatty acids. Heat dissociates the lipids and glycerol is expelled by urine. 3-fatty acids as energy units are easily used by the body and as other poly-unsaturated oils are eliminated via lymphatic (which can take a few weeks) and hepatic systems. In contrast with liposuction and its modifications, this method preserves the structural tissues, acting only on the fat cells. Furthermore, it generates a fibroelastic retraction which can reduce skin flaccidity by up to 50%. This later effect is produced by a partial denaturisation of the extra cellular matrix. The treatment also acts on the fibrotic tracts typical of cellulites returning the strength and flatness to the skin.

The procedures followed in the present invention are as follows: The area of treatment is marked to differentiate by depth and approximate volume ($cm^3$) of excess adipose tissues. The area of treatment is (sterilized) disinfected. The insertion sites are marked. The patient is placed on sterile surrounding and local anesthesia is applied to the skin where there are going to be insertion sites. A small entry is made and the site is widened and pre-tunneled into the subcutaneous tissue by using a small, curved hemostat. A blunt infusion catheter is then inserted via this tunnel into the site, and tumescent anesthetic is delivered first to the deepest layer in a radial fashion and then successively more superficially. Infiltration of the anesthetic is then achieved by pump. A needle is selected according to the fiber diameter and inserted (e.g., 18

G French for 600 um fibers on large areas and 25 G French with a 220 um fiber for face treatments) and a sterile optical fiber is then inserted. The appropriate treatment mode and the parameters of the laser are selected, e.g., as in Table 1. The position of the fiber tip is controlled by the laser aiming beam. The pre-selected energy is applied and the fiber is moved to treat the desired area. Ultrasound guidance can be used to position the tip of the fiber. After all of the entry sites are treated, ultrasound and lymphatic drainage post-procedures are followed. Elastic bandage is placed on the treated area for 3 to 5 days.

This treatment (in contrast with liposuction) preserves the structural tissues and elasticity of the skin with the addition of localized retraction and firming of the area. This reduces flaccidity by up to 50%

In general after the first 72 hours of treatment, there is a considerable edema requiring ultrasound detection and lymphatic drainage. During the first 2 weeks, edema is reduced by around 80% and skin retraction appears. From 2 to 5 weeks, lymphatic edema disappears as well as the delimitation of the treated area. As a general observation, tissues on the treated area appeared more compacted with less irregularity on the surface and better elasticity, and the body shape improves continually and no additional changes are noted after about 40 to 60 days following the procedure.

Low power 980 nm laser is used to treat areas with cellulites. Results are permanent because the adiposite cells are destroyed. Only in very rare exceptions, these cells are reproduced as a side effect: after the laser application, a softening of the treated area appeared to the tact and harder limiting section on the limits of the treated area. This generates a lymphatic edema produced by the body to eliminate the emulsified fat after the procedure.

Figure 1A:
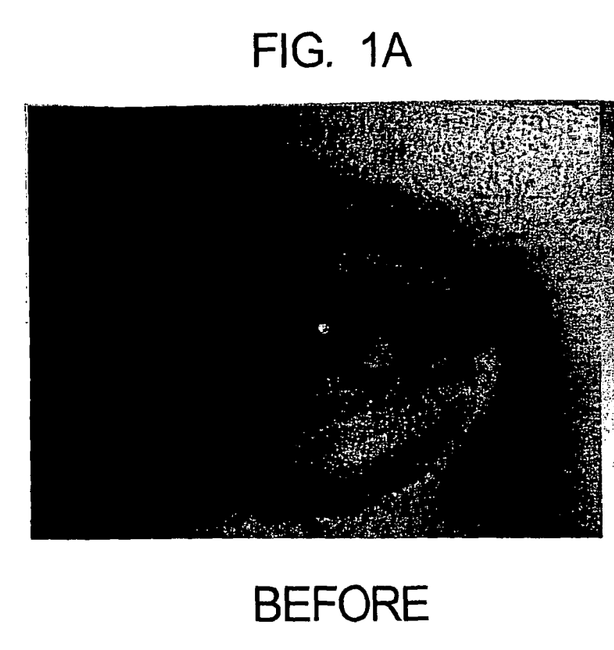
FIGS. 1A and 1B illustrate by photographs the before and after appearance of lower eyelids treated by the method and device of the present invention as an example of the effective treatment provided by the present invention.
Figure 1B:
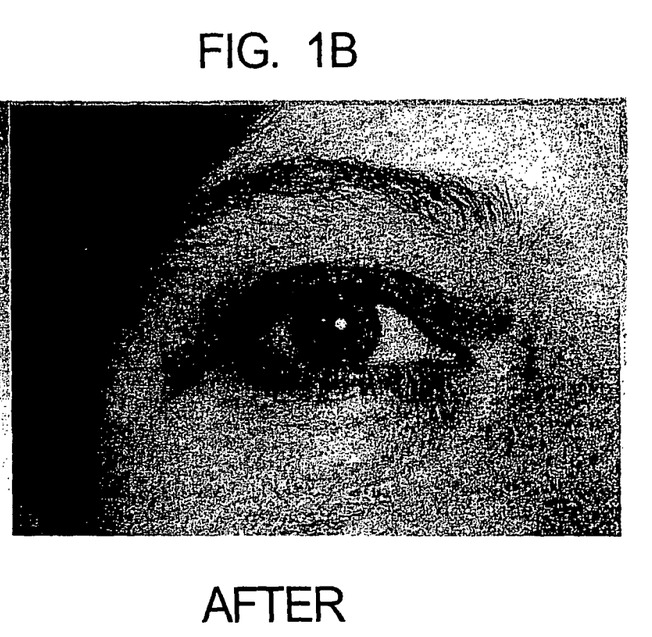
Figure 5A:
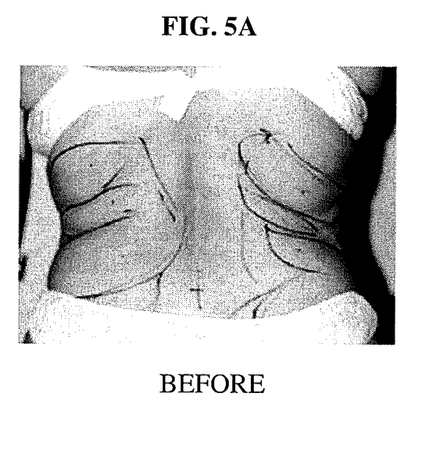
FIGS. 5A and 5B illustrate by photographs the before and after appearance of the dorsal area treated by the method and device of the present invention as an example of the effective treatment provided by the present invention.
Figure 5B:
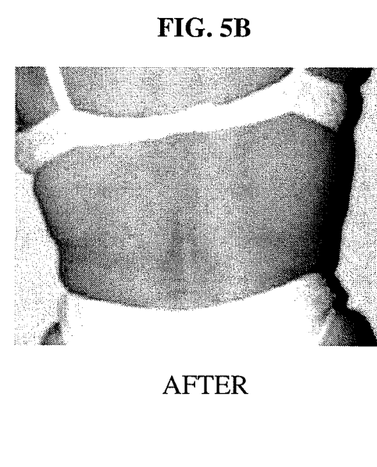

As to the success of the present invention, FIGS. 1A to 1B disclose pictures before and after of the interior eyelids; FIGS. 5A and 5B disclose pictures before and after of a thorax area; and FIGS. 6A and 6B disclose before and after pictures of the thigh and buttock area.

Figure 2:
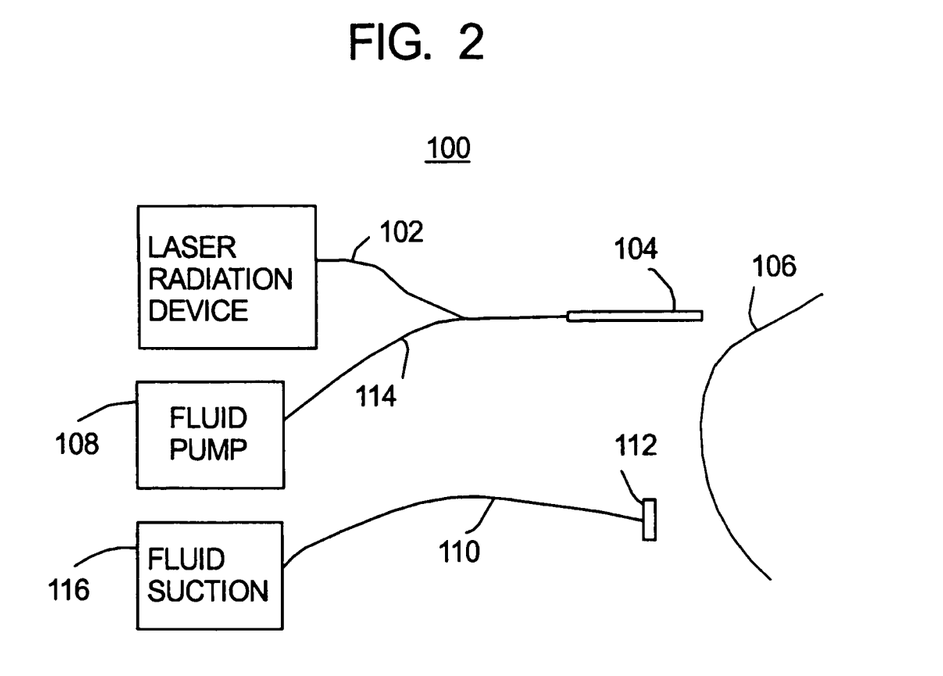
FIG. 2 illustrates by schematic, devices of the present invention.

FIG. 2 shows laser radiation device 100 having optical fiber cable 102 connected into needle-like device 104 that is for insertion into treatment area 106. Fluid pump 108 is used for inputting any fluids including the tumescent anesthetic fluid and the saline solution through line 114 into and through the needle like device 104. After treatment, a fluid suction pump 116 having one or more hoses 110 with one or more suction heads 112 is placed on the entry sites to assist in the removal of liquid from the area of treatment.

Figure 3A:
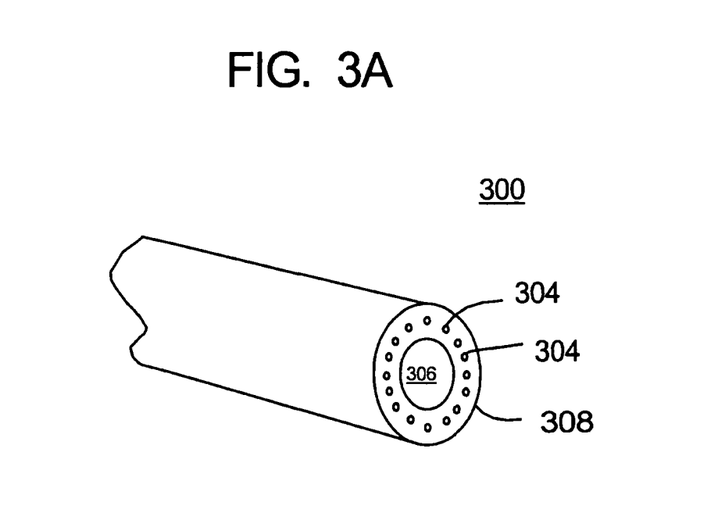
FIGS. 3A and 3B illustrate by a cross sectional elevational view, two different embodiments of the needle like device of the present invention.
Figure 3B:
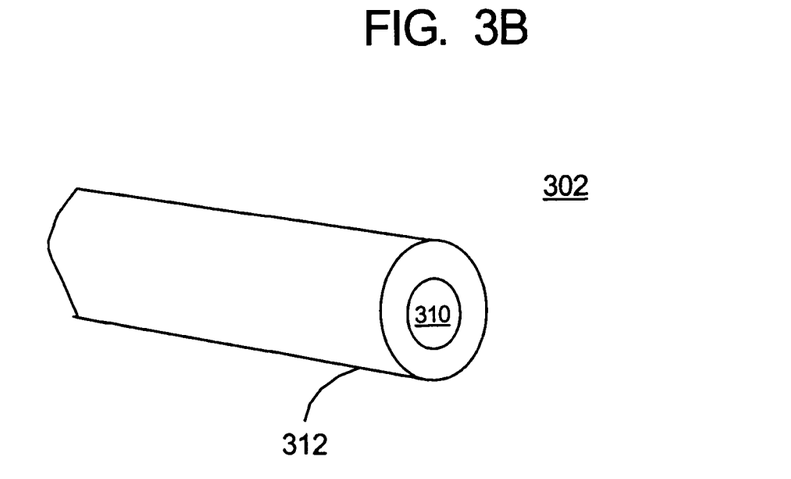

As to needle like device 104, several embodiments are shown in FIGS. 3A and 3B as needles 300 and 302. The entry ends are appropriately finished. As seen in FIG. 3A, needle 300 being in cross section has a plurality of optical fibers 304 circumferentially located about central lumen 306 which may be used for inputting fluids and for suction removal of fluids. Wall 308 surrounding fibers 304 may act as a cladding and whole needle 300 may be manufactured from a single preform of material appropriately formed. FIG. 3B illustrates by cross section another needle like device 302 wherein a lumen 310 is centrally located in optical fiber 312 being a core fiber without any cladding shown. Appropriate cladding layer(s), buffer layer(s), and protective layer(s), although not shown, are understood to be present as needed.

Figure 4:
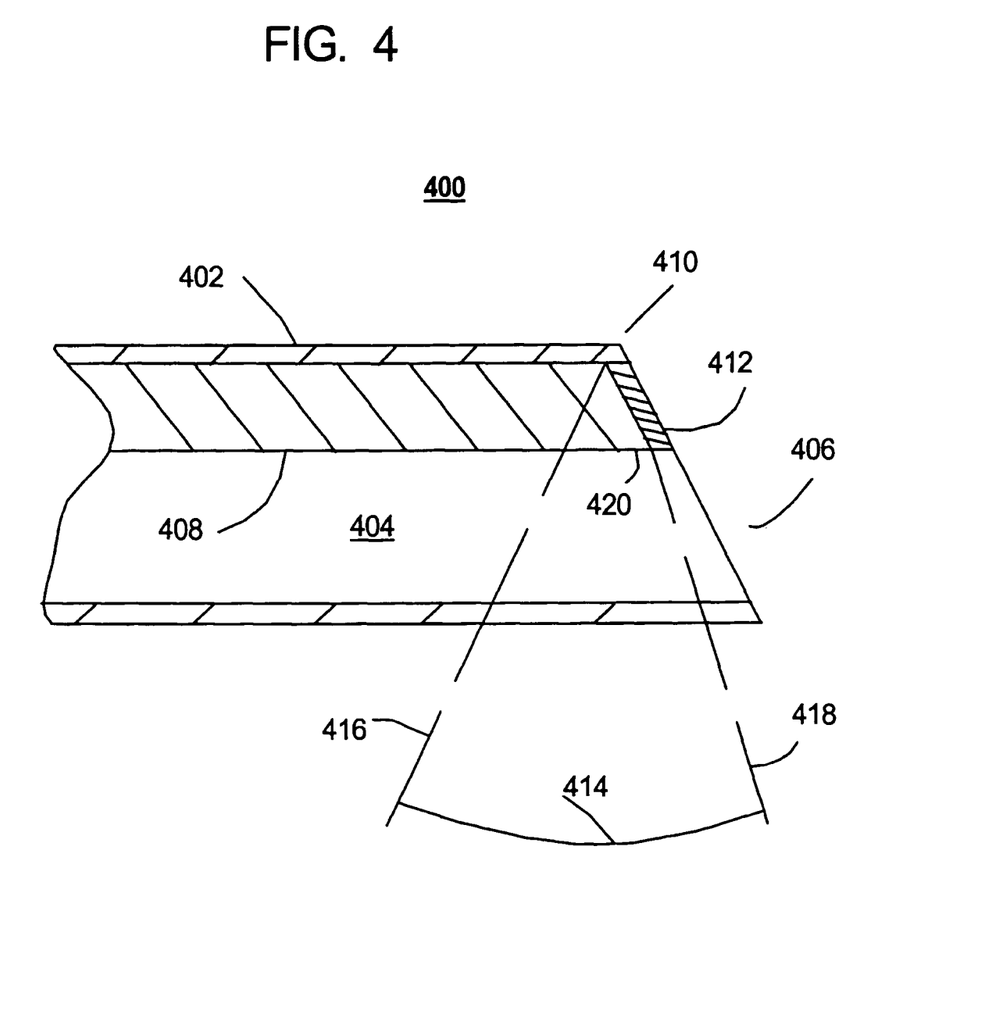
FIG. 4 illustrates by a cross sectional elevational view, an optical fiber in a cannula for the present invention.

FIG. 4 further illustrates another embodiment of a needle like device 400 wherein cannula wall 402 has central lumen 404 therein. Tip area 406 is appropriately formed as a slanted wedge. Inside of lumen 404 is attached either separately or integrally formed optical fiber 408. Tip area 410 of optical fiber 406 is formed to have slanted output end 420 with mirror 412 formed thereon to cause optical radiation 414 to be output in a sidewise manner as shown between rays 416 and 418. Mirror 412 formed on tip 420 need not have a surface congruent with the surface of tip 406 of cannula wall 402. Alternatively, instead of adding mirror 412, end is angled at the critical angle for reflection and the light exits fiber 406 perpendicularly to the fiber axis. Due to the closeness of the adipose tissue to the skin surface, a catheter or similar device may not be needed to guide the needle to area of treatment 106, shown in FIG. 2. That is only the entering needle is needed to introduce the optical fiber to the fatty area to be treated.

FIGS. 7A to 7F illustrate various devices for applying radiation, inputting fluids and removing fluids from an area of treatment within the body. The device 700A comprises a cannula 702 with an end 704 fitted with an applicator tip 706A. Cannula 700 has one or more lumens for holding one or more laser optical fibers 708 with a side-fire tip 710. An elongated aperture 712 is located along the traverse axis of application tip 706A. Side-fire tip 710 is positioned within lumen 714 so as to allow the radiation output from side-fire tip 710 to exist through aperture 712. The length of aperture 712 is several times the width of aperture 712 so as to allow a sufficient space for outputting and inputting fluid therethrough.

Figure 7A:
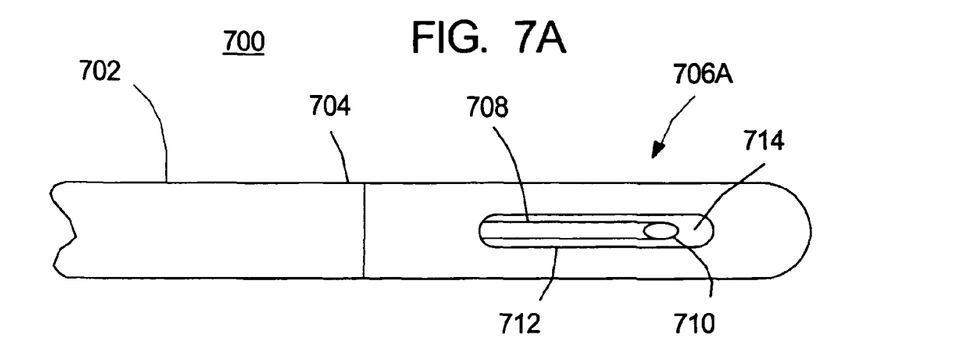
FIGS. 7A to 7F illustrate different devices for the application of laser radiation and the removal of liquid from the area of treatment.
Figure 7B:
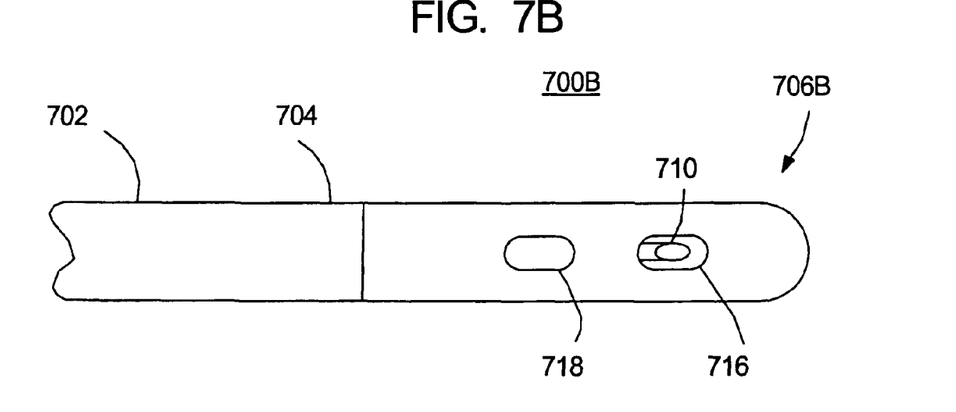

In FIG. 7B, applicator tip 706 has a first aperture 716 for radiation output from side-fire tip 710 and a second aperture 718 for inputting and removing fluids. Further, there may be multiple apertures 718 on applicator tip 706B and further there may be separate apertures for inputting fluid and removing fluid appropriately located about tip 706.

Figure 7C:
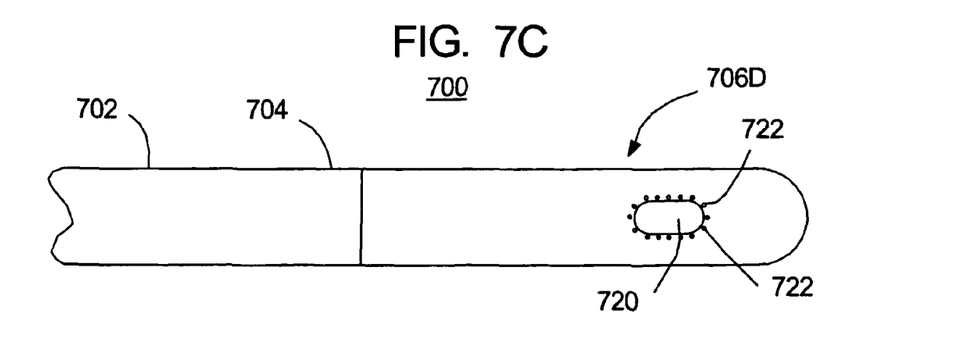

In FIG. 7C, applicator tip 706C has one aperture 720 for the control of fluids. Located about aperture 702 are a plurality of optical fiber outputs 722.

Figure 7D:
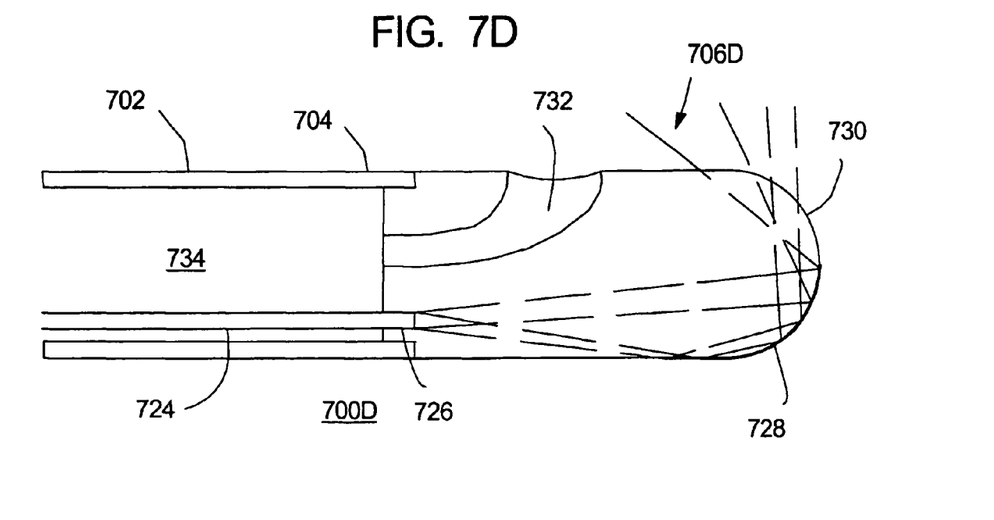

In FIG. 7D, applicator tip 706D is attached to cannula end 704. An optical fiber 724 is placed within one lumen of cannula 702 and has an output tip 726 that directly communicates with applicator tip 706D. Applicator tip 706D is made from high quality optical silica, for example, and has a reflective coating 728 positioned on a portion of the front end 730 so as to intercept output radiation from optical fiber 724 and reflect such in a radial direction as shown. Further application tip 706D may include at least one lumen 732 therein that communicates with one lumen 734 in cannula 702.

Figure 7E:
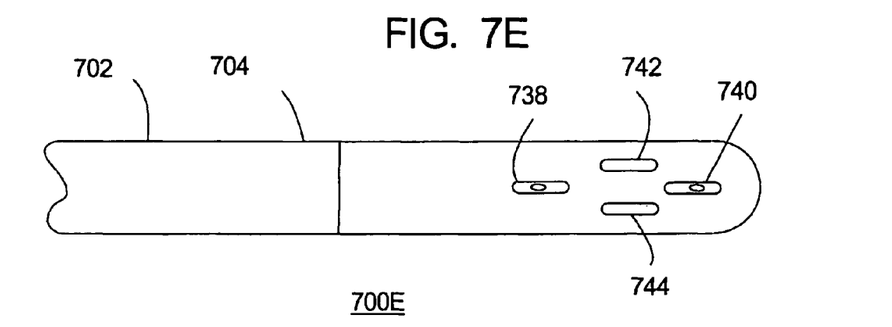

FIG. 7E discloses another embodiment where applicator tip 700E has two laser output apertures 738 and 740 and two fluid control apertures 742 and 744. Although this shows these located on the same side of the tip 700E, other locations are equally feasible, for example, having the output apertures located on the opposite of the tip 700E. Further, additional apertures may be included about the tip so as to reduce or eliminate the need for rotating the cannula 702 when outputting radiation and/or controlling fluid.

Figure 7F:
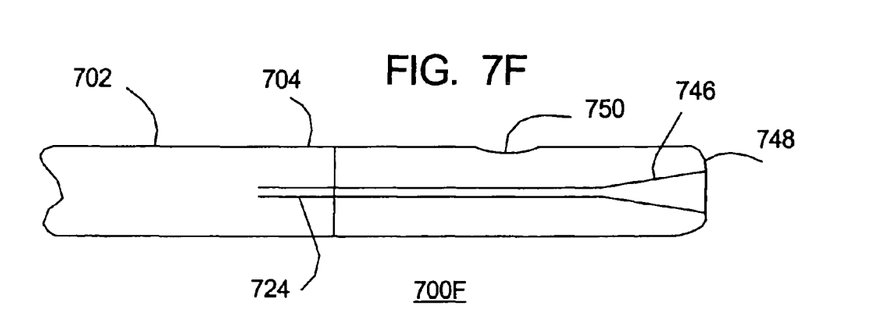

FIG. 7F discloses another embodiment of applicator tip 700F where optical fiber 724 has a wedge shaped termination 746 to spread the radiation from a front end 748. One or more fluid control apertures 750 are included in applicator tip 700E.

The present invention is further illustrated by the following examples, but is not limited thereby. Table 1 illustrates the various parameters used in operating the diode laser of the present invention to remove excess adipose tissues in the areas noted:

TABLE 1

|  | Power [W] | Time [sec] | Energy [Joules] | Nr. Of pulses |
|---|---|---|---|---|
| Lower eyelids | 4 watts | 2 sec | 8 J | 20–30 |
| Facial | 6 watts | 3 sec | 18 J | 40–70 |
| Collar | 7 watts | 3 sec | 21 J | 40–70 |
| Thorax | 12 watts | 3 sec | 36 J | 70+ |
| Abdomen | 15 watts | 2 sec | 30 J | 70+ |
| Thigh & buttock | 12 watts | 3 sec | 16 J | 70+ |

Furthermore, this treatment is an out-patient alternative, minimally invasive, more elegant and with less risks and complications than current treatments. Although there is no need for hospitalization, it must be followed by a diet and physical ultrasound and lymphatic drainage. Results can be appreciated from about week 3 and final results achieved between weeks 6 and 10.

EXAMPLE 1

FIGS. 1A and 1B illustrate by photographs the before and after appearance of lower eyelids treated by the method and device of the present invention as example of effective treatment of the present invention.

The laser energy is delivered through a disposable fiber optic directly into the sub-dermal tissue. This tissue is composed of adiposities and structural tissues irrigated by small arteries, veins and lymphatic. In the lower eyelids, the laser is pulsed 20 to 30 times at a power of 4 W delivering 8 Joules at 2 seconds per pulse.

The radiation of the Biolitec® 980 nm laser is selectively absorbed by the sub-dermal tissue which is surrounded by saline solution. By thermal effect (980 nm radiation is highly absorbed by water) the adipose membranes are destroyed. For example, using 15 watts for 3 seconds (45 Joules) the temperature reached on the tip of the fiber is around 100° C. which is transmitted by the tumescent anesthesia diffusing and reducing the temperature to 70° C.±10° C. It is thus considered that a minimum temperature of 50° C. must be present to denature the cells' proteins and preferably the temperature of the cells being treated is in the range of 70° C.±10° C. Moving the laser fiber back and forth, a 2 cm penetration with fat tissues dissociation is achieved.

EXAMPLE 2

FIGS. 5A and 5B illustrate by photographs the before and after appearance of the dorsal area treated by the method and device of the present invention as an example of effective treatment of the present invention.

The laser energy is delivered through a disposable fiber optic directly into the sub-dermal tissue. This tissue is composed by adiposities and structural tissues irrigated by small arteries, veins and lymphatic. In the thorax area, the laser is pulsed more than 70 times at a power of 12 watts, 36 Joules at 3 seconds per pulse.

The radiation of the Biolitec® 980 nm laser is selectively absorbed by the sub-dermal tissue which is surrounded by saline solution. By thermal effect (980 nm radiation is highly absorbed by water) the adiposities membranes are destroyed. For example, using 15 watts for 3 seconds (45 Joules) the temperature reached on the tip of the fiber is around 100° C. which is transmitted by the tumescent anesthesia diffusing and reducing to 70° C.±10° C. the temperature. It is thus considered that a minimum temperature of 50° C. should be present to denature the cells' proteins and preferably the temperature of the cells being treated is in the range of 70° C.±10° C. Moving the laser fiber back and forth, a 2 cm penetration with fat tissues dissociation is achieved.

EXAMPLE 3

Figure 6A:
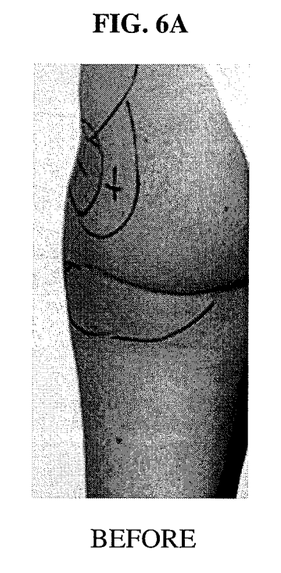
FIGS. 6A and 6B illustrate by photographs the before and after appearance of the external side of the thigh treated by the method and device of the present invention as an example of the effective treatment provided by the present invention.
Figure 6B:
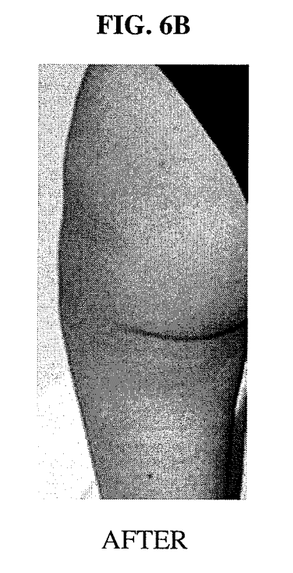

FIGS. 6A and 6B illustrate by photographs the before and after appearance of the external side of the thigh treated by the method and device of the present invention as an example of effective treatment of the present invention.

The laser energy is delivered through a disposable fiber optic directly into the sub-dermal tissue. This tissue is composed by adiposities and structural tissues irrigated by small arteries, veins and lymphatic. In the thigh and buttock area, the laser is pulsed at least 70 times at a power of 15 watts, 30 Joules at 2 seconds per pulse The radiation of the Biolitec® 980 nm laser is selectively absorbed by the sub-dermal tissue which is surrounded by saline solution. By thermal effect (980 nm radiation is highly absorbed by water) the adiposities membranes are destroyed. For example, using 15 watts for 3 seconds (45 Joules) the temperature reached on the tip of the fiber is around 100° C. which is transmitted by the tumescent anesthesia diffusing and reducing the temperature to 70° C.±10° C. It is thus considered that a minimum temperature of 50° C. should be present to denature the cells' proteins and preferably the temperature of the cells being treated is in the range of 75° C.±25° C. Moving the laser fiber back and forth, a 2 cm penetration with fat tissues dissociation is achieved.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. A method of reducing localized lipodystrophies and flaccidity and of simultaneous collagen reformation for improving cosmetic appearance of a subject comprising the steps of:
   a. defining an area of treatment on said subject;
   b. preparing at least one insertion site in said area for minimally invasive entry;
   e. applying laser radiation to adipose tissue in said area of treatment to break the cell membranes;
   f. applying post treatment procedures to said area of treatment;
   g. wherein positioning of said optical fiber is performed using ultrasound.

2. The method of reducing localized lipodystrophies and flaccidity according to claim 1 wherein said operating parameters of said diode laser are dependent upon said area of treatment, said operating parameters including: power, length of treatment, energy and number of pulses.

3. The method of reducing localized lipodystrophies and flaccidity according to claim 1 wherein a liquid is input into said area of treatment, said liquid being heated by the diode laser to provide heat to said area of treatment.

4. The method for reducing localized lipodystrophies and flaccidity according to claim 3 wherein said liquid is a saline solution.

5. The method of reducing localized lipodystrophies and flaccidity according to claim 4 wherein the adipose tissue under treatment reaches a temperature in the range of 75° C.±25° C.

6. The method of reducing localized lipodystrophies and flaccidity according to claim 1 wherein said post treatment includes lymphatic drainage, ultrasound, site drainage from a needle entry or application of one or more elastic bandages.

7. The method of reducing localized lipodystrophies and flaccidity according to claim 6 further including the application of external suction.

8. The method of reducing localized lipodystrophies and flaccidity according to claim 1 further including removing liquefied cellulite tissues by suction.

9. The method of reducing localized lipodystrophies and flaccidity according to claim 1, wherein said area of treatment is selected from the areas consisting of interior eyelid, face, collar, thorax, abdomen, thigh and buttock.

10. The method of reducing localized lipodystrophies and flaccidity according to claim 1 further including inputting a tumescent anesthesia into said area.

11. The method of reducing localized lipodystrophies and flaccidity according to claim 1 wherein the needle-like device comprises a plurality of optical fibers located circumferentially about the central lumen.

12. The method of reducing localized lipodystrophies and flaccidity according to claim 1 wherein the needle-like device comprises a central lumen within a fiber optic core.

13. The method of reducing localized lipodystrophies and flaccidity according to claim 1 wherein the diode laser produces laser radiation having a wavelength of 980 nm.

14. A method of reducing localized lipodystrophies and flaccidity and of simultaneous collagen reformation for improving cosmetic appearance of a subject comprising the steps of:
   a. defining an area of treatment on said subject;
   b. preparing at least one insertion site in said area for minimally invasive entry;
   c. selecting operating parameters for an diode laser based upon said area of treatment;
   d. inputting a liquid into said area of treatment, said liquid providing heating to said area of treatment, said liquid being heated by said diode laser to provide a broader source of heat;
   e. inserting and positioning a needle-like device comprising a wall defining a central lumen and at least one optical fiber attached to the inside of said lumen, wherein a distal tip of the optical fiber defines a slanted output end with a mirror formed thereon;
   f. applying selectively laser radiation to adipose tissue in said area of treatment to break the cell membranes; and
   g. applying post treatment procedures to said area of treatment;
   h. wherein positioning of said optical fiber is performed using ultrasound.

15. The method of reducing localized lipodystrophies and flaccidity according to claim 14, wherein said laser radiation is at 980 nm.

16. The method of reducing localized lipodystrophies and flaccidity according to claim 14 wherein said operating parameters of said diode laser are dependent upon said area of treatment, said operating parameters including: power, length of treatment, energy and number of pulses.

17. The method for reducing localized lipodystrophies and flaccidity according to claim 14 wherein said liquid is a saline solution.

18. The method of reducing localized lipodystrophies and flaccidity according to claim 17 wherein the adipose tissue under treatment reaches a temperature in the range of 75° C.±25° C.

19. The method of reducing localized lipodystrophies and flaccidity according to claim 14 wherein said post treatment includes lymphatic drainage, ultrasound, site drainage from a needle entry or application of one or more elastic bandages.

20. The method of reducing localized lipodystrophies and flaccidity according to claim 19 further including the application of external suction.

21. The method of reducing localized lipodystrophies and flaccidity according to claim 14 further including removing liquefied cellulites tissues by suction.

22. The method of reducing localized lipodystrophies and flaccidity according to claim 14 further including inputting a tumescent anesthesia into said area.

23. The method of reducing localized lipodystrophies and flaccidity according to claim 14, wherein said area of treatment is selected from the areas consisting of interior eyelid, face, collar, thorax, abdomen, thigh and buttock.

* * * * *